(12) United States Patent
Sharma et al.

(10) Patent No.: US 10,194,855 B2
(45) Date of Patent: Feb. 5, 2019

(54) APPARATUS AND METHOD FOR MEASUREMENT OF FLOW RATE OF CEREBROSPINAL FLUID IN A CONDUIT

(71) Applicant: Indian Institute of Technology Bombay, Mumbai, Maharashtra (IN)

(72) Inventors: Gaurav Ravi Sharma, Mumbai (IN); Tarkeshwar Chandrakant Patil, Mumbai (IN); Siddhartha Prakash Duttagupta, Mumbai (IN); Shreyas Shyamsunder, Mumbai (IN); Javed Yunus Sheikh, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 1200 days.

(21) Appl. No.: 14/299,414

(22) Filed: Jun. 9, 2014

(65) Prior Publication Data
US 2015/0119719 A1  Apr. 30, 2015

(51) Int. Cl.
*A61B 5/00* (2006.01)
*A61B 5/03* (2006.01)
*A61M 27/00* (2006.01)

(52) U.S. Cl.
CPC ............ *A61B 5/4076* (2013.01); *A61B 5/032* (2013.01); *A61B 5/407* (2013.01); *A61M 27/006* (2013.01)

(58) Field of Classification Search
CPC ....... A61B 5/032; A61B 5/407; A61B 5/4076; A61M 27/006
See application file for complete search history.

(56) References Cited

U.S. PATENT DOCUMENTS

| | | | | |
|---|---|---|---|---|
| 5,772,261 A | * | 6/1998 | Magram | A61M 27/002 285/242 |
| 2006/0020239 A1 | * | 1/2006 | Geiger | A61B 5/0031 604/9 |
| 2008/0013291 A1 | * | 1/2008 | Bork | A61B 5/032 361/748 |

* cited by examiner

*Primary Examiner* — Christopher Cook

(74) *Attorney, Agent, or Firm* — McCarter & English, LLP; David R. Burns

(57) ABSTRACT

Apparatuses and methods for measurement of flow rate of cerebrospinal fluid in a conduit are provided. The apparatus comprises a heating element mounted on the conduit, the heating element arranged for heating the CSF flowing through the conduit for generating bubbles. The apparatus further comprises two optical sensing devices mounted sequentially on the conduit and downstream from the heating element. The first optical sensing device and the second optical sensing device are separated by a predetermined device interval. Both the first and the second optical sensing devices comprise an optical emitter and an optical detector. The apparatus further comprises a processing device coupled to the optical sensing devices, wherein the signals from the optical sensing devices are transmitted to the processing device for detection of bubbles, resulting in the detection of the flow velocity. The bubble size can be optimized by applying ultrasonic waves or thermal energy.

14 Claims, 11 Drawing Sheets

APPARATUS AND METHOD FOR MEASUREMENT OF FLOW RATE OF CEREBROSPINAL FLUID IN A CONDUIT

RELATED APPLICATION

This application claims priority under 35 U.S.C. § 119 to Indian Patent Application No. 3334/MUM/2013, filed on Oct. 24, 2013. The entire content of the foregoing application is explicitly incorporated herein by reference.

TECHNICAL FIELD OF INVENTION

The invention generally relates to a method and apparatus for measuring the flow rate of body fluids, and more specifically for measuring the flow rate of cerebrospinal fluid in a shunt tube implanted inside the body.

BACKGROUND OF THE INVENTION

Hydrocephalus causes accumulation of cerebrospinal fluid (CSF) in the ventricles of the brain, which expands as a result. This pressurizes the brain tissues and causes headaches, vomiting, nausea, papilledema, sleepiness or coma. Therefore, a shunt tube is surgically inserted to drain away the excess CSF. However, the shunt tube internally develops blockage with time, which eventually stops the flow of CSF, which can have disastrous consequences. One solution for the above problem is to surgically replace the entire shunt tube. This involves the inconvenience of a major surgery and the exorbitant charges associated with the surgery. A measurement of the flow rate of the CSF in the shunt tube can forecast blockage of the shunt tube, thus providing opportunities for preventive medical resolution of the situation and thus reducing any likelihood of serious consequences for the patient.

Conventional systems include an apparatus for measuring quantitative CSF flow in shunt tubes implanted under the skin. The system includes an array of thermosensors clustered in three sections, cooling device, placed on the skin surface and an associated data acquisition and analysis device. The method of measuring flow rate of CSF involves assessing thermal properties of skin and measuring CSF flow in shunt tubing. The indirect measurement of the flow rate of CSF leads to inaccuracy in measurements.

SUMMARY

According to an aspect of the invention, an apparatus for measurement of flow velocity of cerebrospinal fluid (CSF) in a conduit is disclosed. The apparatus comprises a heating element mounted on the conduit, wherein the heating element is arranged for heating the CSF flowing through the conduit for generating bubbles. The apparatus further comprises a first optical sensing device and a second optical sensing device mounted sequentially on the conduit and downstream from the heating element. The first optical sensing device and the second optical sensing device are separated by a predetermined device interval. The first optical sensing device comprises a first optical emitter and a first optical detector. The second optical sensing device comprises a second optical emitter and a second optical detector. The apparatus further comprises a processing device coupled to the first optical sensing device and the second optical sensing device, wherein the signals from the first optical detector and the second optical detector are transmitted to the processing device for detection of bubbles. The detection of bubbles is performed by detecting a change in the collection of electromagnetic waves by the first optical detector and the second optical detector. When in use, the processing device measures a first time point and a second time point at which a bubble within the bubbles is detected by the first optical sensing device and the second optical sensing device respectively for deducing flow velocity of the cerebrospinal fluid carrying the bubbles between the first optical sensing device and the second optical sensing device. The predetermined device interval is stored in the processing device.

According to another aspect of the invention, a method for measurement of flow velocity of cerebrospinal fluid in a conduit is disclosed. The first step comprises generating bubbles by heating the cerebrospinal fluid flowing through the conduit, wherein the heating is performed by a heating element mounted on the conduit. The next step is detecting a bubble within the bubbles by a processing device from signals transmitted from a first optical detector of a first optical sensing device and recording a first time point. The first optical sensing device is mounted on the conduit and downstream from the heating element. The first optical sensing device comprises a first optical emitter and the first optical detector. The detection of the bubble is performed by detecting a change in the collection of electromagnetic waves by the first optical detector. The next step comprises detecting the bubble by the processing device from signals transmitted from a second optical detector of a second optical sensing device and recording a second time point. The second optical sensing device is mounted on the conduit and downstream from the first optical sensing device. The second optical sensing device comprises a second optical emitter and a second optical detector. The first optical sensing device and the second optical sensing device are separated by a predetermined interval. The detection of the bubble is performed by detecting a change in the collection of electromagnetic waves by the second optical detector. The next step is calculating flow velocity of the cerebrospinal fluid carrying the bubbles between the first optical sensing device and the second optical sensing device. The processing device measures time points a bubble within the bubbles is detected by the first optical sensing device and the second optical sensing device. The predetermined interval is stored in the processing device.

BRIEF DESCRIPTION OF DRAWINGS

Exemplary embodiments of the present invention are described hereinafter with reference to the following drawings, in which.

DETAILED DESCRIPTION

There are many benefits of the apparatuses and methods for measurement of flow rate of cerebrospinal fluid in a conduit described herein. One of the benefits include reducing inconvenience to the person when trying to clear an obstruction in a shunt tube. Another one is to detect obstructions in a shunt tube. Another benefit includes finding the location of an obstruction in a shunt tube, and forecasting the development of an obstruction in a shunt tube.

Figure 1:
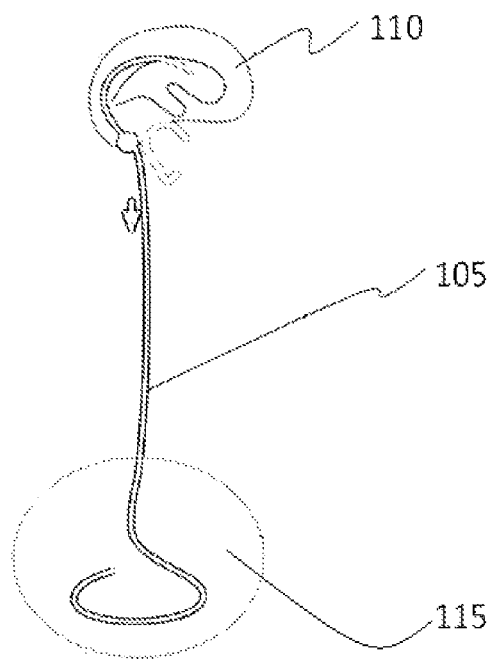
FIG. 1 shows a schematic illustration of a shunt tube implanted in a body of a hydrocephalic person to drain the excess cerebrospinal fluid (CSF)

FIG. 1 shows a schematic illustration of a shunt tube 105 implanted in a body of a hydrocephalic person. The shunt tube 105 is implanted in the body by means of a surgery performed on the person. The shunt tube 105 extends from a brain 110 of the person to an abdominal cavity 115 of the person and enables draining the excess CSF. As illustrated in FIG. 1, the shunt tube 105 extends along a spinal column of the person and ends in the abdominal cavity 115. In other words, the shunt tube 105 is a nanochannel for carrying the CSF. The draining of the excess CSF by the shunt tube 105 relieves pressure due to accumulation of CSF in the brain or the cerebral region of the hydrocephalic person. The shunt tube 105 is made of silicone.

The shunt tube 105 is segmented into a plurality of sub-units along the complete length of the shunt tube, the sub-units joined with each other to provide a continuous channel for the flow of CSF. Each sub-unit is referred to as a conduit. Both the shunt tube and the sub-units are cylindrical in cross-section. The advantage of having the shunt tube 105 divided into the plurality of sub-units is that, in the event of an obstruction in the shunt tube 105, the particular sub-unit in which the obstruction is present can be replaced instead of replacing the entire shunt tube 105. Replacing the entire shunt tube 105 results in significant inconvenience to the person in terms of undergoing a major surgical procedure.

Figure 2:
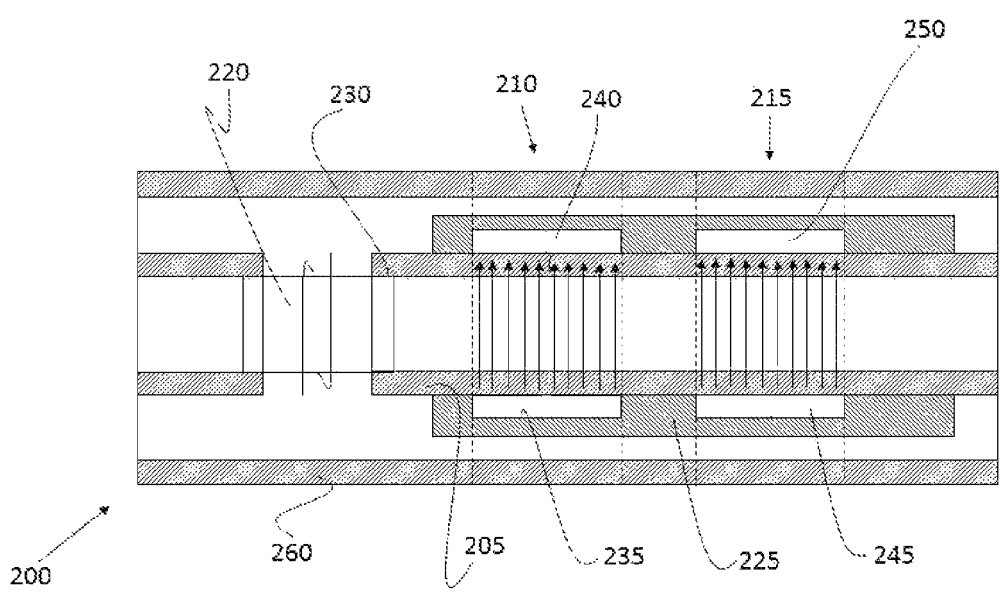
FIG. 2 shows a schematic illustration of a first apparatus for measurement of flow velocity of cerebrospinal fluid in a conduit

FIG. 2 shows a schematic illustration of a first apparatus 200 for measurement of flow velocity of CSF in a conduit 205, the apparatus 200 comprising a first optical sensing device 210 and a second optical sensing device 215. The exemplary embodiment illustrated in FIG. 2 comprises two optical sensing devices. The number of optical sensing devices is not limited to two and can be more than two as well. An exemplary embodiment with three optical sensing devices will be explained hereinafter. As illustrated in FIG. 2, the apparatus 200 also comprises a heating element 220 and a processing device 225.

The heating element 220 is mounted on the conduit 205 on one end 230 of the conduit 205. The conduit 205 is cylindrical in cross-section. The heating element 220 comprises a cylindrical element composed of stainless steel. The cylindrical element is fastened externally to an internal surface of the conduit 205. The internal surface of the conduit 205 has a radius of 2 mm in this example. However, the radius is not limited to 2 mm and can be any other value as well. The cylindrical element has an internal cavity extending along an axis of the cylindrical element through which the CSF flows and drains into the conduit 205. The cylindrical element of one apparatus 200 also enables fastening a conduit of an adjacent apparatus 200, so as to join a plurality of apparatuses 200, as described earlier. The cylindrical element is therefore also referred to as a joint. To elaborate, unfastening the cylindrical element from the conduit on either side separates the adjacent fastened conduits. The fastening method can involve adhesive, which is understood by a person skilled in the art. The cylindrical element is coated with epoxy paste. Epoxy paste is an electrical insulator and a thermal conductor. The cylindrical element can be made of metal, silicone, ceramic or glass. The cylindrical element and the conduit 205 can have varying outer diameters. For example, the cylindrical element can have an outer diameter greater than an outer diameter of the conduit 205. Alternatively, the cylindrical element can have the outer diameter lesser than the outer diameter of the conduit 205. The heating element further comprises a heating coil wound around the cylindrical element coated with epoxy paste, such that the heating coil is wound over the epoxy paste. The advantage of coating the cylindrical element with epoxy paste lies in utilizing the above mentioned insulating property of the epoxy paste to prevent any electrical short between the wound heating coil. The heating coil is composed of nichrome. The nichrome coil can have a length between 45 cm and 55 cm. In one embodiment, the nichrome coil can have a length of 50 cm. The nichrome coil can have a resistance between 4.0Ω and 5.0Ω. In one embodiment, the nichrome coil can have a resistance of 4.9Ω. However, the length and the resistance can be any other value as well.

It is understood by the person skilled in the art that nichrome is an alloy composed of Ni (73.4% to 76.9%), Mn (1%), Fe (1%), Si (1% to 1.5%), Cr (20% to 23%), C (0.1%). Upon passing current through the heating coil, heat is produced by Joule heating and the epoxy paste coated on the cylindrical element dissipates the heat produced to the cylindrical element, which in turn heats the CSF flowing through the internal cavity of the cylindrical element. The heat transferred to the CSF enables generation of bubbles in the CSF flowing through. The heat energy that is transferred from the coil to the fluid is given by $$H = mc_p dT \qquad \text{a.}$$

where m is the mass of the fluid that receives heat a. $c_p$ is the specific heat capacity of the fluid b. dT is the change in temperature required to generate bubbles.

For CSF, it has been observed that a heat energy of 0.2 J to 1 J is required to generate bubbles. During the generation of bubbles, the CSF in the cylindrical element is heated to a temperature of around 45° C. to 50° C. The heating coil wound around the heating element is supplied with intermittent power to generate bubbles. For example, the heating coil is provided with 0.6 mA of current for 1 minute or 0.4 mA of current for 90 seconds. The above are merely exemplary and other combinations of amperage and time are also possible. The providing of power to the heating coil is controlled by a suitable algorithm in the processing device. The processing device can be any suitable small-sized and compact microcontroller with storage capabilities, which will be understood by the person skilled in the art. The bubbles generated are microbubbles, which is understood by the person skilled in the art. The diameter of the microbubbles generated is around $1/10^{th}$ of the hydraulic diameter of the conduit. This provides the advantage of preventing any clogging of the conduit by the generation and flow of bubbles.

As illustrated in FIG. 2, the apparatus 200 further comprises a first optical sensing device 210 and a second optical sensing device 215. The first optical sensing device 210 and the second optical sensing device 215 are mounted adjacent and sequentially on the conduit 205 and downstream from the heating element 220. Downstream refers to the direction of flow of CSF through the heating element 220 and the conduit 205. The first optical sensing device 210 and the second optical sensing device 215 are mounted on the conduit 205 such that the first optical sensing device 210 and the second optical sensing device 215 are attached or fastened on an external surface of the conduit. The mounting of the first optical sensing device 210 and the second optical sensing device 215 will be explained further hereinafter, when describing the components of the first optical sensing device 210 and the second optical sensing device 215. The first optical sensing device 210 and the second optical sensing device 215 are separated by a predetermined device interval, which is also referred to as a first device interval. To elaborate, the first device interval is the distance between a center of the first optical sensing device 210 and a center of the second optical sensing device 215. The distance between the above centers is measured along an imaginary line parallel to an axis of the conduit 205.

Figure 3:
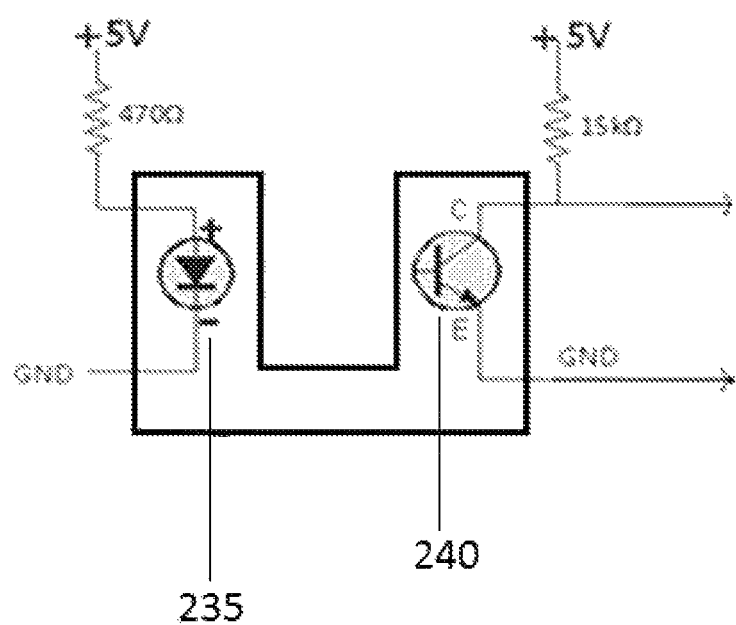
FIG. 3 shows a schematic of an optical emitter and an optical detector in the optical sensing device

The first optical sensing device 210 comprises a first optical emitter 235 and a first optical detector 240, as illustrated in FIG. 3 and the second optical sensing device 215 comprises a second optical emitter 245 and a second optical detector 250. FIG. 3 shows a schematic of the optical emitter 235 and the optical detector 240 and the same circuit components applies to any optical sensing device, described above and hereinafter. DC power is supplied to circuit of the optical emitter 235. A 470Ω resistor is arranged to limit the current flowing through the emitter circuit. A 15 kΩ resistor is arranged to bias the detector in the detector's active region. The detector referred to in FIG. 3 is a phototransistor. The phototransistor collector voltage changes with change in media between the emitter and the detector, which is described hereinafter. The circuit shown in FIG. 3 is just an example and different combinations of the circuit components like resistors can be used. Different combinations of the circuit components will provide differing results, which can be understood by the person skilled in the art. The optical sensing devices, namely the first optical sensing device 210 and the second optical sensing device 215 enable detecting the presence of at least one bubble in the CSF flowing through the conduit 205. It is understood by the person skilled in the art that the conduit 205 which is a sub-unit of the shunt tube 105 is transparent, making optical detection or sensing of bubbles possible. The reason for using bubbles for detecting flow velocity of CSF is because CSF is a clear and colorless fluid with an optical density equal to one, making the flow of CSF difficult to detect. The flow rate of CSF in the conduit 205 and in the shunt tube 105 is in the range of microliters per minute to nanoliters per minute. The flow rate of CSF varies among humans.

Each of the optical emitters, namely the first optical emitter 235 and the second optical emitter 245 comprise an infrared emitter. The emitter is in the form of an LED and the working wavelength of the emitter and the detector is any suitable wavelength range suitable for in-vivo conditions. An example of such wavelength is 820 nm. Each of the optical detectors, namely the first optical detector 240 and the second optical detector 250 comprise a phototransistor. In one embodiment, each of the optical sensing devices comprise a U-shaped slot with opposite ends, the optical emitter and the optical detector disposed on the opposite ends of the U-shaped slot. The U-shaped slot has a cavity in which the conduit 205 is arranged to be housed. Upon housing the conduit 205 in the cavity of the U-shaped slot, the optical emitter and the optical detector of the optical sensing device are disposed on opposite ends of the diameter of the conduit 205. In an alternative embodiment, the optical emitter and the optical detector are merely mounted or fastened by suitable means on the conduit 205 such that the optical emitter and the optical detector are situated at diametrically opposite ends, without the U-shaped slot.

The apparatus 200 further comprises a processing device 225 coupled to the first optical sensing device 210 and the second optical sensing device 215. The coupling mentioned above is electronic in nature. More specifically, the processing device 225 is a circuit board on which the optical sensing devices are mounted directly. The signals from the first optical detector 240 and the second optical detector 250 are transmitted to the processing device 225 for digitally processing the signals for the purpose of detecting the bubbles. The detection of bubbles is performed by a change in the collection of electromagnetic waves and specifically, infrared waves by any of the optical detectors, namely the first optical detector 240 and the second optical detector 250, which will be described hereinafter.

The processing device 225 is arranged to measure a first time point $t_1$ and a second time point $t_2$ at which a bubble or a set of bubbles within the bubbles generated by the heating element 220 is detected by the first optical sensing device 210 and the second optical sensing device 215 respectively. The time points, $t_1$ and $t_2$ and the first device interval between the first optical sensing device 210 and the second optical sensing device 215 enable deducing the flow velocity of the CSF carrying the bubble or the set of bubbles between the first optical sensing device 210 and the second optical sensing device 215. The first device interval is stored in the processing device 225.

The apparatus 200 can further comprise a cylindrical sleeve or a jacket 260 for enclosing the conduit 205 with the heating element 220, the first optical sensing device 210, the second optical sensing device 215 and the processing device 225. The sleeve 260 serves as a protective cover for the conduit 205 with the components indicated above. The jacket is made of silicone.

Figure 4:
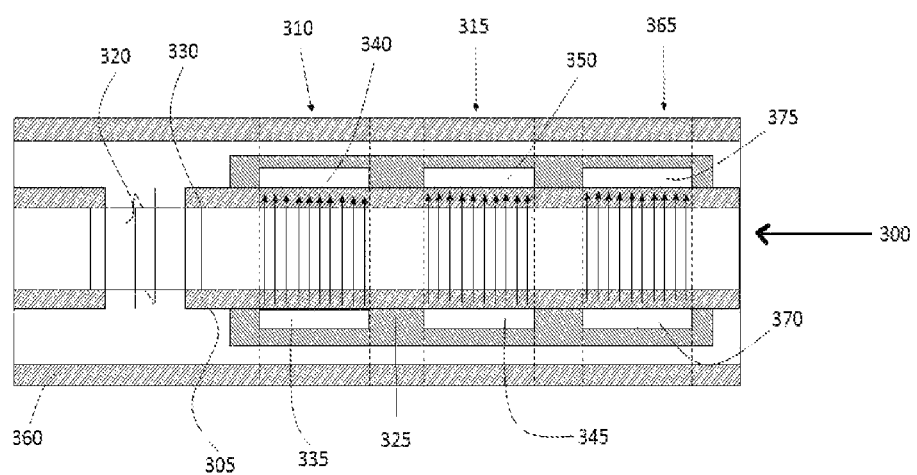
FIG. 4 shows a schematic illustration of a second apparatus for measurement of flow velocity of cerebrospinal fluid in a conduit

FIG. 4 shows a schematic illustration of a second apparatus 300 for measurement of flow velocity of CSF in a conduit 305. The difference between the first apparatus 200 and the second apparatus 300 is that the first apparatus 200 comprises two optical sensing devices, whereas the second apparatus 300 comprises three optical sensing devices. The difference in functioning between the first apparatus 200 and the second apparatus 300 will be described hereinafter. As described earlier, the first apparatus 200 and the second apparatus 300 are exemplary apparatuses and there can be more than three optical sensing devices arranged in an apparatus for measurement of flow velocity of CSF.

As illustrated in FIG. 4, the apparatus 300 comprises a heating element 320 mounted on one end 330 of the conduit 305. The heating element 320 is structurally and functionally the same as the heating element 220 of the first apparatus 200. The apparatus 300 further comprises a first optical sensing device 310 and a second optical sensing device 315.

The first optical sensing device 310 comprises a first optical emitter 335 and a first optical detector 340. The second optical sensing device 315 comprises a second optical emitter 345 and a second optical detector 350. The first optical sensing devices 310 and 210 are structurally the same and function the same way. The second optical sensing devices 315 and 215 are structurally the same and function the same way. The apparatus 300 further comprises a processing device 325 which is also structurally and functionally same to the processing device 225 of the apparatus 200. The structure and function of the coupling of the processing device 325 to the first optical sensing device 310 and the second optical sensing device 315 is the same as the structure and function of the coupling of the processing device 225 to the first optical sensing device 210 and the second optical sensing device 215. The powering of the components of the apparatus 300 is also the same as the powering of the components of the apparatus 200.

Moreover, the apparatus 300 further comprises a third optical sensing device 365 disposed on the conduit, mounted by any one of the methods described above with respect to apparatus 200. The third optical sensing device 365 is disposed adjacent the second optical sensing device 315 and downstream from the second optical sensing device 315. The third optical sensing device 365 is separated from the second optical sensing device 315 by another predetermined device interval, which is also referred to as the second device interval. The first device interval separates the first optical sensing device 310 and the second optical sensing device 315. The second device interval can be the same as the first device interval. Alternately, the second device interval can be different from the first device interval. In any case, the first device interval and the second device interval are stored in the processing device 325. To elaborate, the first device interval is the distance between a center of the first optical sensing device 310 and a center of the second optical sensing device 315. Likewise, the second device interval is the distance between a center of the second optical sensing device 315 and a center of the third optical sensing device 365. The distance between the above centers is measured along an imaginary line parallel to an axis of the conduit 305.

The third optical sensing device 365 comprises a third optical emitter 370 and a third optical detector 375. The third optical emitter 370 is the same structurally and functionally to the optical emitters mentioned above. The third optical detector 375 is the same structurally and functionally to the optical detectors mentioned above. The processing device 325 is further arranged to deduce flow velocity of the CSF carrying bubbles between the second optical sensing device 315 and the third optical sensing device 365, which will be explained hereinafter. The processing device 325 is further arranged to compare the flow velocity between the first optical sensing device 310 and the second optical sensing device 315 and the flow velocity between the second optical sensing device 315 and the third optical sensing device 365 to determine the presence of any obstruction in the conduit 305, which will be explained hereinafter. The apparatus 300 can also comprise a cylindrical sleeve or jacket 360, the structure and the function of which is the same as the cylindrical sleeve or jacket 260. The cylindrical sleeve 360 is composed of silicone.

The method of deducing flow velocity between two points and determining the presence of any obstruction is described hereinafter with respect to the method of measurement of flow velocity of CSF in the conduit.

Figure 5:
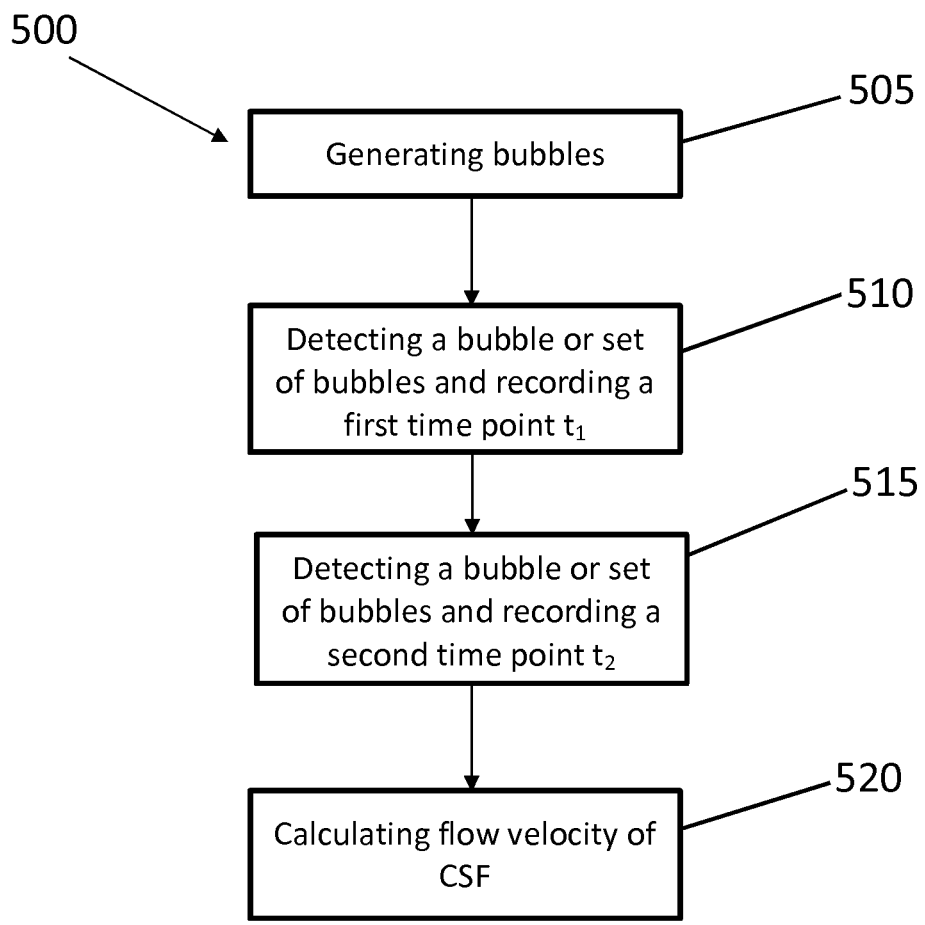
FIG. 5 shows the process steps for a method of measurement of flow velocity of CSF in a conduit

FIG. 5 shows the process steps for a method 500 of measurement of flow velocity of CSF in the conduit 205 or conduit 305. To elaborate, the process steps of the method 500 is not limited to be used only for the apparatus 200 and 300, but can also be used for similar structures.

The method 500 comprises a first method step 505 for generating bubbles. Generating bubbles is performed by heating the CSF flowing through the conduit 205 or 305 by the heating element 220 or 320, which has been explained above. The method 500 comprises a further method step 510 for detecting a bubble or a set of bubbles within the bubbles generated in step 505 and recording a first time point $t_1$, the bubbles disposed between the optical detector and the optical emitter of the first optical sensing device 210 and 310. The detection of bubbles is performed by the processing device 225 or 325 from the signals transmitted from the first optical detector 240 or 340. The principle behind the detection of the set of bubbles is done by detecting a change in the collection of electromagnetic waves by the first optical detector 240 or 340. The detection of the set of bubbles by any of the optical sensing devices will be described below.

The IR waves when travelling through a liquid medium or CSF are absorbed more when compared to travelling through a rarer medium like low density water vapor. Hence, the amount of IR waves reaching the IR detector from the IR emitter after passing through a denser medium like liquid or CSF is less than the amount of IR waves reaching the IR detector after passing through a rarer medium like low density water vapor. When there are no bubbles disposed between the optical emitter and the optical detector, more IR waves are absorbed by the CSF. With bubbles disposed between the IR emitter and the IR detector, the absorption of the IR waves is reduced, thus enabling more IR waves to reach the IR detector, resulting in a higher voltage generated by the detector. The higher voltage is because more photons are collected by the optical detector or phototransistor thus increasing the voltage generated at the optical detector.

Figure 6:
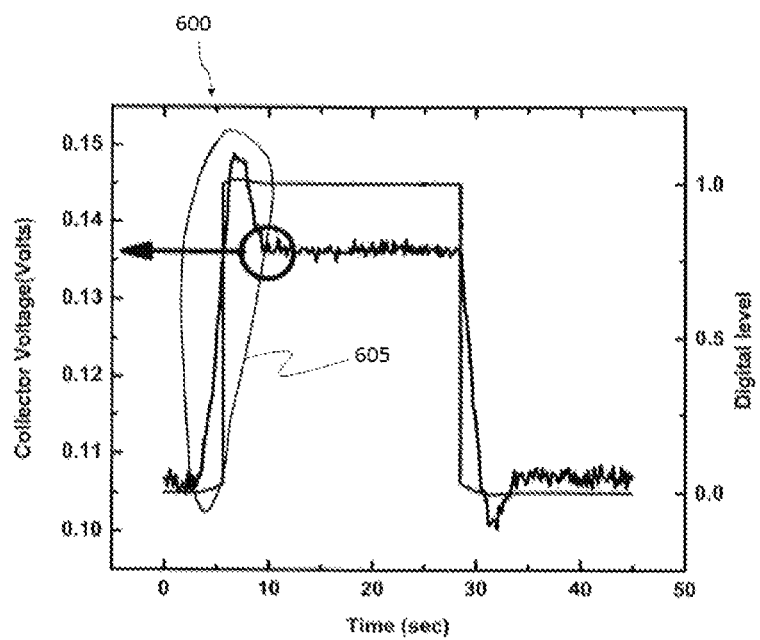
FIG. 6 shows an exemplary waveform for detecting the presence of bubbles in CSF

FIG. 6 shows an exemplary waveform 600 for detecting the presence of bubbles in CSF. The voltage at the collector or the optical detector is represented on the Y-axis and the time is represented on the X-axis. As explained above, as soon as a bubble or a set of bubbles moves away from or out of a position in between the optical emitter and the optical detector, the voltage at the collector reduces and the waveform shows a fall in the voltage. The bubbles generated in the CSF flow comprise low density water vapor. Likewise, as soon as a bubble or a set of bubbles moves into a position between the optical emitter and the optical detector, the voltage at the collector increases sharply and the waveform shows a steep rise. Therefore, a spike or a rising edge in the waveform indicates the presence of an air gap, which is a bubble. The intensity and the slope of the voltage rise in the waveform is a result of the size of the bubble, the number of bubbles and the orientation of a set of bubbles. FIG. 6 illustrates a voltage rise or a spike 605 which indicates the presence of a bubble or a set of bubbles. The waveform is transmitted to the processing device 225 or 325 and is processed by signal processing algorithms stored in the processing device 225 or 325.

The method 500 comprises a further method step 515 for detecting the bubble or the set of bubbles with the bubbles generated in step 505 and recording a second time point $t_2$, the bubbles now disposed between the optical detector and the optical emitter of the second optical sensing device 215 and 315. The detection of the bubble or the set of bubbles is the same as explained above.

The next step in the method 500 is a method step 520 for calculating flow velocity of the CSF carrying the bubbles between the first optical sensing device 210 or 310 and the second optical sensing device 215 or 315, which is performed by the processing device 225 or 325. The processing device 225 or 325 measures time points the bubble or the set of bubbles is detected by the first optical sensing device 210 or 310 and the second optical sensing device 215 or 315, which is explained hereinafter.

In step 510, the processing device 225 or 325 records a first time point $t_1$ at which the bubble or the set of bubbles are detected by the first optical sensing device 210 or 310. In the step 515, the processing device 225 or 325 records a second time point $t_2$ at which the bubble or the set of bubbles are detected by the second optical sensing device 215 or 315. Since the first device interval is known, the first device interval divided by the difference between $t_1$ and $t_2$ results in the flow velocity of the CSF between the first optical sensing device 210 or 215 and the second optical sensing device 310 or 315.

Figure 7:
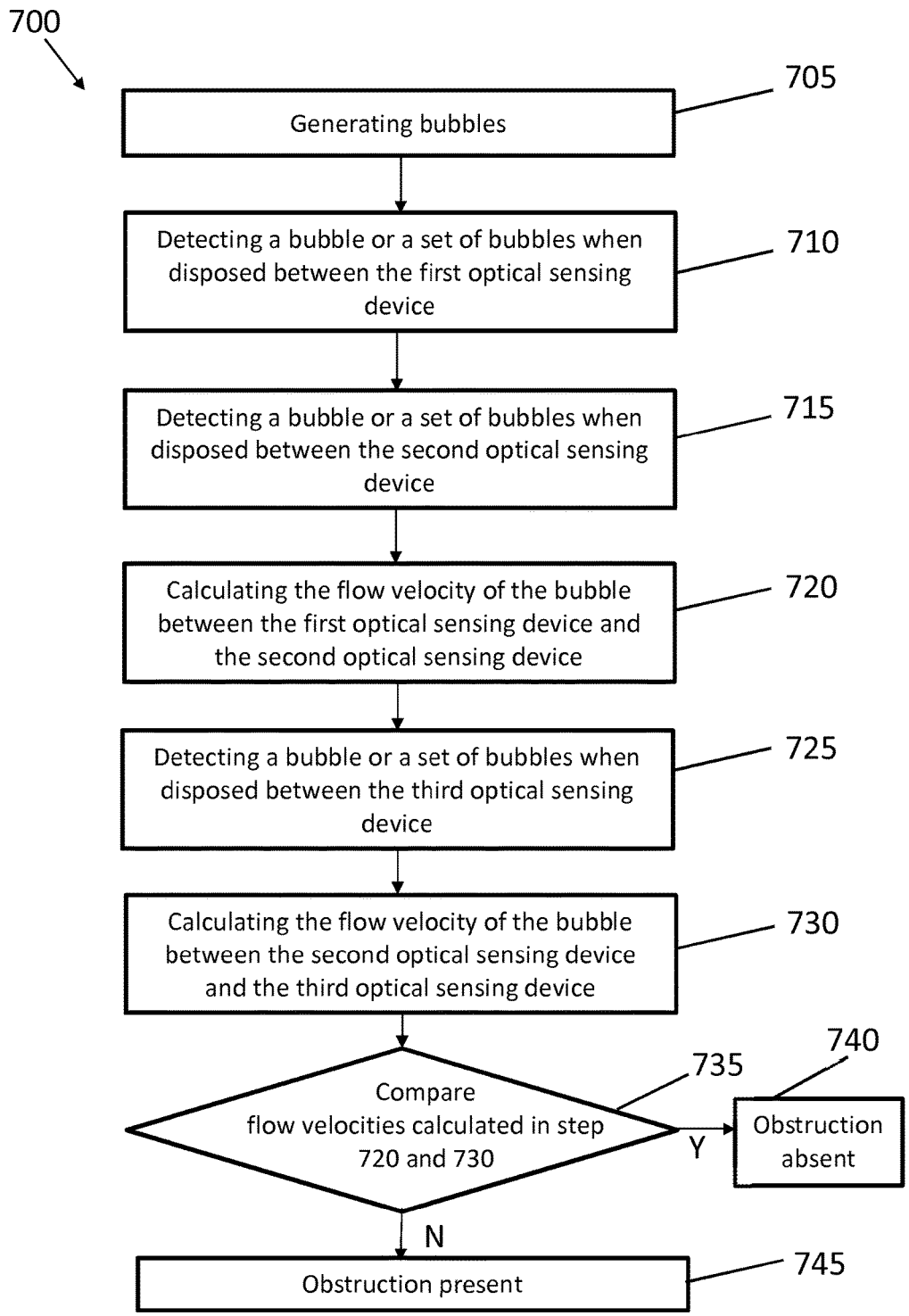
FIG. 7 shows the process steps for a method of measurement of flow velocity of CSF in a conduit with three optical sensing devices and subsequent detection of obstruction in the conduit

FIG. 7 shows the process steps for a method 700 of measurement of flow velocity of CSF in a conduit with three optical sensing devices and subsequent detection of obstruction in the conduit. To elaborate, the process steps as illustrated in FIG. 7 is not limited to be used only for the apparatus 300, but can also be used for similar structures having three or more optical sensing devices.

The method 700 comprises a method step 705 for generating bubbles, a method step 710 for detecting a bubble or a set of bubbles within the generated bubbles when disposed between the first optical sensing device 310, a method step 715 for detecting the bubble or the set of bubbles within the generated bubbles when disposed between the second optical sensing device 315 and a method step 720 for calculating the flow velocity of the bubble or the set of bubbles between the first optical sensing device and the second optical sensing device. The calculated velocity is depicted as $v_{1\text{-}2}$. The process of the method steps 705, 710, 715 and 720 are the same as the process of the method steps 505, 510, 515 and 520 which have already been explained above.

The method 700 comprises a further method step 725 for detecting the bubble or the set of bubbles within the bubbles generated in the method step 705 when the bubbles move in between the third optical emitter 370 and the third optical detector 375 of the third optical sensing device 365 by the processing device 325 and for recording a third time point $t_3$. The process of the method step 725 is the same as the process of the method steps 510 and 515, which have already been explained above.

The method 700 comprises a further method step 730 for calculating the flow velocity of CSF between the second optical sensing device 315 and the third optical sensing device 365. The calculated flow velocity is $v_{2\text{-}3}$. The process of the method step 730 is the same as what has already been explained for method step 520, except that in this method step time point $t_2$ and $t_3$ are utilized.

The method 700 comprises a further method step 735 for comparing the flow velocities calculated in the method steps 720 and 730 by the processing device 325. The comparison of the flow velocities $v_{1\text{-}2}$ and $v_{2\text{-}3}$ is targeted at determining if there is an obstruction anywhere in the vicinity of the first optical sensing device 310, the second optical sensing device 315 and the third optical sensing device 365. If the flow velocities $v_{1\text{-}2}$ and $v_{2\text{-}3}$ are uniform, then there is no obstruction as depicted in block 740 in FIG. 7. If the flow velocities $v_{1\text{-}2}$ and $v_{2\text{-}3}$ are not uniform, then there is an obstruction as depicted in block 745 in FIG. 7. The principle by which obstruction is determined by comparing velocities is described below.

Figure 8:
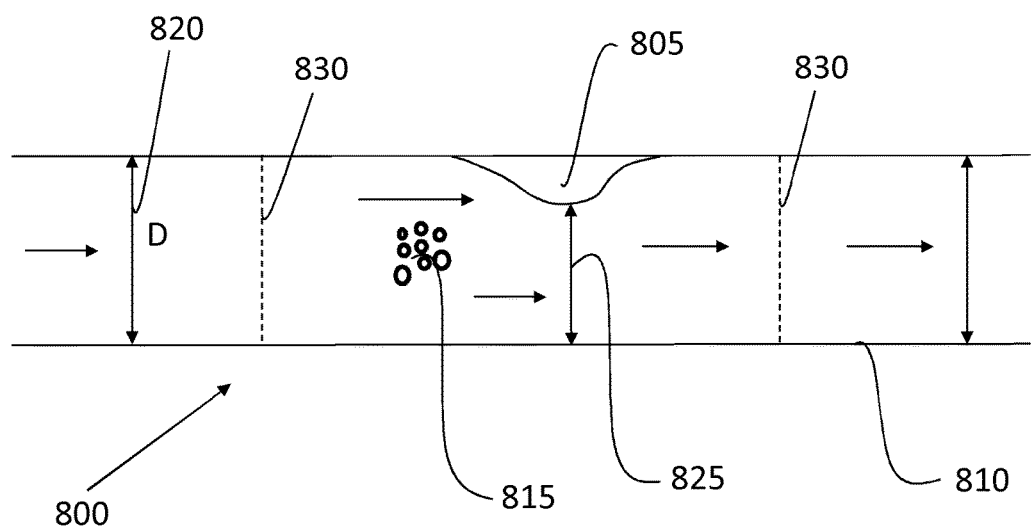
FIG. 8 shows a schematic illustration of an obstruction in a conduit carrying CSF and generated bubbles

FIG. 8 shows a schematic illustration of an obstruction 805 in a conduit 810 carrying CSF and generated bubbles 815. The obstruction 805 depicted is purely exemplary and the obstructions in the conduit can take any form and shape. The obstructions can be partial or even complete. In the case of a complete obstruction the flow of CSF is fully blocked and there will be no flow of the CSF in the conduit. The obstruction which is described on the basis of the apparatus and the method here is a partial obstruction and can be visualized as a constriction or a partial blockage. The conduit 810 has a diameter 820 depicted by D, which is the normal diameter or the unobstructed diameter. At the obstruction 805, the conduit 810 has a diameter 825 depicted by d. The CSF flow is from left to right for the purposes of explanation only and is depicted by the arrow marks in FIG. 8. Generally, a fluid flow in pipes and channels and in this case flow of CSF in the conduit is governed by venturi effect. According to venturi effect, the fluid pressure and flow velocity are inversely proportional. Therefore, the unconstricted or unobstructed sections of the conduit 810 where the diameter is D has a higher pressure than constricted or obstructed sections of the conduit 810 where the diameter is d. Hence, the flow velocity of the unconstricted or unobstructed sections of the conduit 810 where the diameter is D is lower than the constricted or obstructed sections. In short, a higher flow velocity indicates an obstruction.

FIG. 8 also illustrates a zone bound by imaginary lines 830 on both sides of the obstruction 805 in which the velocity is higher when compared to the velocity outside of the zone. Even inside the zone, the velocity is highest near the center of the obstruction 805 and gradually tapers down towards the imaginary lines 830. Beyond the imaginary lines 830, the velocity of flow is normal. The gradient of flow velocity in the zone is a function of the size and shape of the obstruction.

Applying this flow velocity variation to the apparatus 300, in the event of an obstruction anywhere between the first optical sensing device 310 and the second optical sensing device 315, the flow velocity will be higher in the zone between and around the first optical sensing device 310 and the second optical sensing device 315 and normal elsewhere. Hence $v_{1\text{-}2}$ will be higher than $v_{2\text{-}3}$ and hence in method step 735, the processing device 325 will determine that the obstruction is somewhere between the first optical sensing device 310 and the second optical sensing device 315. Likewise, in the event of an obstruction anywhere between the second optical sensing device 315 and the third optical sensing device 365, the flow velocity will be higher in the zone between and around the second optical sensing device 315 and the third optical sensing device 365 and normal elsewhere. Hence $v_{2\text{-}3}$ will be higher than $v_{1\text{-}2}$ and hence in method step 735, the processing device 325 will determine that the obstruction is somewhere between the second optical sensing device 315 and the third optical sensing device 365.

Moreover, the obstruction can occur at any point in the conduit 205 or 305. The obstruction can be anywhere in between two optical sensing devices or can also be within the boundaries of any optical sensing device. So, detection of flow velocity in the vicinity of any optical sensing device that is greater than the flow velocities in the vicinity of the adjacent optical sensing devices indicates the existence of an obstruction somewhere near the former.

The accuracy with which an obstruction can be detected depends on the device interval between the optical sensing devices such as the first device interval and the second device interval. The lesser the device interval, the greater the capacity of the apparatus to capture even small changes in the reduction of the flow velocity, thus indicating the presence of an obstruction, resulting in a finer resolution for the apparatus. Moreover, the obstruction can be detected as long as at least one of the detectors out of the detectors involved in measurement of the flow velocity is inside the zone.

With an apparatus having two optical sensing devices such as the apparatus 200, a comparison of flow velocities such as $v_{1-2}$ and $v_{2-3}$ is not possible, but the flow velocity between the first optical sensing device and the second optical sensing device $v_{1-2}$ can be compared with a standard flow velocity of CSF for the particular conduit that is stored in the processing device 325. Hence, even an apparatus with two optical sensing devices such as the apparatus 200 can be used for determining the presence of any obstruction in the conduit.

Apparatuses such as apparatus 200 or apparatus 300 or any apparatus having more than three optical sensing devices can be coupled sequentially to form the shunt tube 105 instead of having one single continuous tube. The advantage of having multiple apparatuses or multiple units is that it allows removal of the obstructed apparatus or unit and replace the removed unit alone rather than removing the complete shunt tube.

Figure 9:
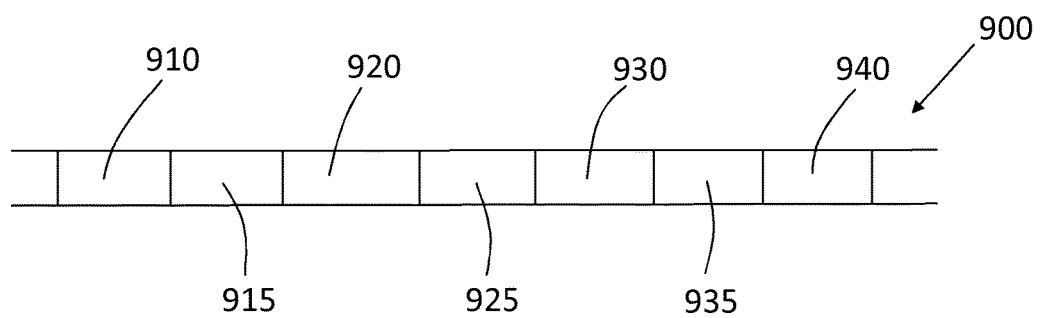
FIG. 9 shows a shunt tube having a plurality of flow units connected to each other

FIG. 9 shows a shunt tube 900 having a plurality of flow units connected to each other. FIG. 9 illustrates the shunt tube 900 comprising a plurality of flow units 910, 915, 920, 925, 930, 935 and 940. The plurality of flow units are coupled with one another to form an elongate channel for carrying cerebrospinal fluid from a cerebral region of the body to a target region of the body for draining the cerebrospinal fluid. The target region of the body can be the abdominal cavity or any other region in the body. Each of the plurality of flow units as described above is arranged to be fastened and unfastened with an adjacent flow unit, so that the flow units can be joined to the shunt tube or removed from it individually. This enables removal of any one of the flow units in case of any obstruction detected as described above. The flow unit can be structurally and functionally the same as the apparatus 200 as described above. Thus, the structural components of the flow units are the same as the structural components of the apparatus 200 and the flow units are capable of performing the method 500. Alternatively, the flow unit can be structurally and functionally the same as the apparatus 300 as described above. Thus, the structural components of the flow units are the same as the structural components of the apparatus 300 and the flow units are capable of performing the method 700.

The information processed by the processing devices 225 and 325 can be transmitted by any suitable in-vivo wireless telemetry apparatus (not shown in Figures), which is understood by the person skilled in the art. The information transmitted by the telemetry apparatus will let the reader or the user of the information know the location of the obstruction.

Figure 10:
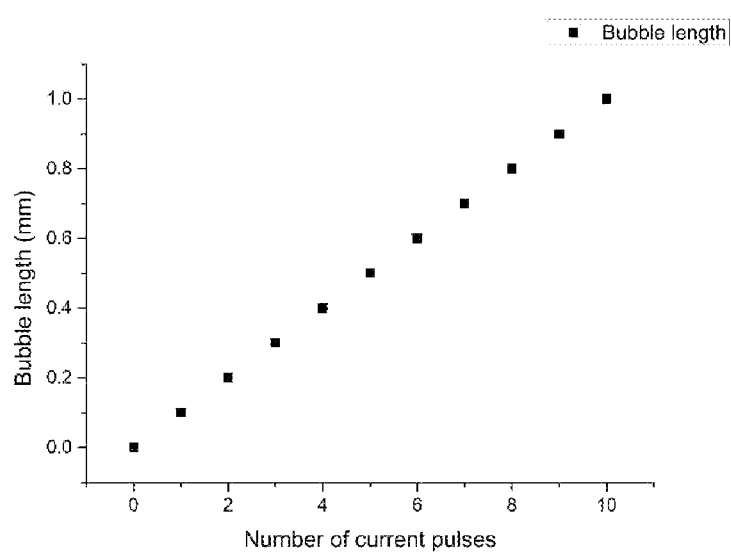
FIG. 10 shows a graphical representation of the relationship between the bubble length and the number of current pulses

The size of the bubbles is tunable, so that large bubbles that can block fluid flow and small bubbles that will not flow with the fluid can be prevented. Bubble sizes can be optimized by two methods. In the first method of bubble size optimization, which is referred to as a thermal method, current pulses or spikes are applied to the heating element 220. The bubble size depends on the number of pulses or spikes provided. These tiny bubbles coalesce and form a large bubble. FIG. 10 shows a graphical representation of the relationship between the bubble length in mm and the number of current pulses. As shown in FIG. 10, the higher the number of pulses, the higher the bubble length.

Figure 11:
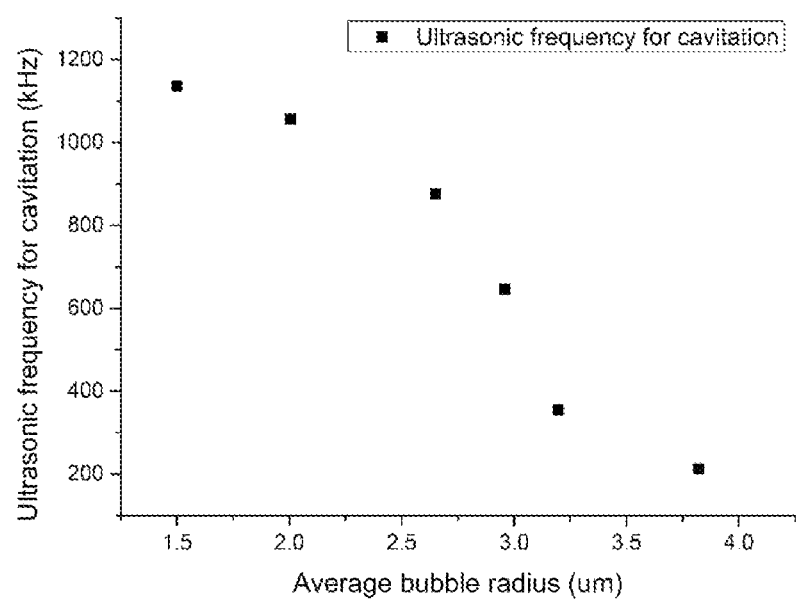
FIG. 11 shows a graphical representation of the relationship between the average bubble radius and the ultrasonic frequency for cavitation

The second method of bubble size optimization is the acoustic method, in which ultrasonic waves are used to produce bubbles by cavitation. The frequency of the ultrasonic waves influences the bubble size. FIG. 11 shows a graphical representation of the relationship between the average bubble radius and the ultrasonic frequency for cavitation, which is inversely proportional. The tiny bubbles coalesce and form a large bubble. The ultrasonic waves are produced by an ultrasound applicator positioned external to the body and proximal to the shunt tube.

It is to be understood that the foregoing description is intended to be purely illustrative of the principles of the disclosed techniques, rather than exhaustive thereof, and that changes and variations will be apparent to those skilled in the art, and that the present invention is not intended to be limited other than as expressly set forth in the following claims.

We claim:

1. An apparatus for measurement of flow velocity of cerebrospinal fluid in a conduit, comprising:
   a heating element mounted on the conduit and arranged for heating the cerebrospinal fluid flowing through the conduit to generate bubbles;
   a first optical sensing device and a second optical sensing device mounted sequentially on the conduit and downstream from the heating element, wherein the first optical sensing device and the second optical sensing device are separated by a predetermined device interval, the first optical sensing device comprising a first optical emitter and a first optical detector and the second optical sensing device comprising a second optical emitter and a second optical detector; and
   a processing device coupled to the first optical sensing device and the second optical sensing device and wherein the signals from the first optical detector and the second optical detector are transmitted to the processing device for detection of bubbles, the detection of bubbles performed by detecting a change in the collection of electromagnetic waves by the first optical detector and the second optical detector;
   wherein, when in use, the processing device measures a first time point and a second time point at which a bubble within the bubbles is detected by the first optical sensing device and the second optical sensing device respectively for deducing flow velocity of the cerebrospinal fluid carrying the bubbles between the first optical sensing device and the second optical sensing device, the predetermined device interval being stored in the processing device.

2. The apparatus for measurement of flow velocity of cerebrospinal fluid in a conduit as claimed in claim 1, wherein the heating element is a nichrome coil having a length between 45 cm to 55 cm and a resistance between $4.0\Omega$ to $5.0\Omega$.

3. The apparatus for measurement of flow velocity of cerebrospinal fluid in a conduit as claimed in claim 1, wherein the first optical emitter and the second optical emitter is an infrared LED emitter.

4. The apparatus for measurement of flow velocity of cerebrospinal fluid in a conduit as claimed in claim 1, wherein the first optical detector and the second optical detector is a phototransistor detector.

5. The apparatus for measurement of flow velocity of cerebrospinal fluid in a conduit as claimed in claim 1, further comprising a cylindrical sleeve for enclosing the heating element, the first optical sensing device, the second optical sensing device and the processing device along a length of the sleeve.

6. The apparatus for measurement of flow velocity of cerebrospinal fluid in a conduit as claimed in claim 1, further comprising a third optical sensing device mounted on the conduit, the third optical sensing device disposed adjacent the second optical sensing device and downstream from the second optical sensing device, the third optical sensing device separated from the second optical sensing device by another predetermined device interval and wherein the processing device is coupled to the third optical sensing device;
   wherein the processing device is further arranged to deduce flow velocity of the cerebrospinal fluid carrying the bubbles between the second optical sensing device and the third optical sensing device by detection of bubbles; and
   wherein the processing device is further arranged to compare the flow velocity between the first optical sensing device and the second optical sensing device and the flow velocity between the second optical sensing device and the third optical sensing device to determine the presence of an obstruction in the conduit.

7. The apparatus for measurement of flow velocity of cerebrospinal fluid in a conduit as claimed in claim 6, further comprising a cylindrical sleeve for enclosing the heating element, the first optical sensing device, the second optical sensing device, the third optical sensing device and the processing device along a length of the sleeve.

8. The apparatus for measurement of flow velocity of cerebrospinal fluid in a conduit as claimed in claim 7, wherein the sleeve is composed of silicone.

9. The apparatus for measurement of flow velocity of cerebrospinal fluid in a conduit as claimed in claim 1, wherein current pulses supplied to the heating element is arranged to determine the size of the generated bubbles.

10. The apparatus for measurement of flow velocity of cerebrospinal fluid in a conduit as claimed in claim 1, further comprising an external ultrasound applicator arranged for supplying ultrasound waves to generate bubbles and wherein the frequency of the ultrasound waves is arranged to determine the size of the generated bubbles.

11. A method for measurement of flow velocity of cerebrospinal fluid in a conduit, the method comprising:
   generating bubbles by heating the cerebrospinal fluid flowing through the conduit, the heating performed by a heating element mounted on the conduit;
   detecting a bubble within the bubbles by a processing device from signals transmitted from a first optical detector of a first optical sensing device and recording a first time point, the first optical sensing device mounted on the conduit and downstream from the heating element, wherein the first optical sensing device comprises a first optical emitter and the first optical detector, the detection of the bubble performed by detecting a change in the collection of electromagnetic waves by the first optical detector;
   detecting the bubble by the processing device from signals transmitted from a second optical detector of a second optical sensing device and recording a second time point, the second optical sensing device mounted on the conduit and downstream from the first optical sensing device, the second optical sensing device comprising a second optical emitter and the second optical detector, wherein the first optical sensing device and the second optical sensing device are separated by a predetermined interval, the detection of the bubble performed by detecting a change in the collection of electromagnetic waves by the second optical detector; and
   calculating flow velocity of the cerebrospinal fluid carrying the bubbles between the first optical sensing device and the second optical sensing device, wherein the processing device measures time points a bubble within the bubbles is detected by the first optical sensing device and the second optical sensing device, and wherein the predetermined interval is stored in the processing device.

12. The method for measurement of flow velocity of cerebrospinal fluid in a conduit as claimed in claim 11, wherein generating bubbles by heating the cerebrospinal fluid comprises generating bubbles by heating the cerebrospinal fluid with a nichrome coil having a length between 45 cm to 55 cm and a resistance between $4.0\Omega$ to $5.0\Omega$.

13. The method for measurement of flow velocity of cerebrospinal fluid in a conduit as claimed in claim 11, wherein the electromagnetic waves is infrared light.

14. The method for measurement of flow velocity of cerebrospinal fluid in a conduit as claimed in claim 11, further comprising:
   detecting the bubble within the bubbles by the processing device from signals transmitted from a third optical detector of a third optical sensing device and recording a third time point, the third optical sensing device mounted on the conduit and disposed adjacent the second optical sensing device and downstream from the second optical sensing device, the third optical sensing device separated from the second optical sensing device by another predetermined device interval and wherein the processing device is coupled to the third optical sensing device, the third optical sensing device comprising a third optical emitter and the third optical detector;
   calculating flow velocity of the cerebrospinal fluid carrying the bubbles between the second optical sensing device and the third optical sensing device; and
   comparing the flow velocity between the first optical sensing device and the second optical sensing device and the flow velocity between the second optical sensing device and the third optical sensing device by the processing device for determining the presence of an obstruction in the conduit.

* * * * *